US008088102B2

(12) United States Patent
Adams et al.

(10) Patent No.: US 8,088,102 B2
(45) Date of Patent: *Jan. 3, 2012

(54) DILATION AND STENT DELIVERY SYSTEM FOR BIFURCATION LESIONS

(75) Inventors: Daniel O. Adams, Orono, MN (US); David J. Blaeser, Champlin, MN (US); Richard C. Mattison, Zimmerman, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 264 days.

This patent is subject to a terminal disclaimer.

(21) Appl. No.: 12/258,883

(22) Filed: Oct. 27, 2008

(65) Prior Publication Data

US 2009/0143854 A1     Jun. 4, 2009

Related U.S. Application Data

(63) Continuation of application No. 10/768,561, filed on Jan. 30, 2004, now Pat. No. 7,445,610, which is a continuation of application No. 09/590,885, filed on Jun. 9, 2000, now abandoned, which is a continuation of application No. 09/035,642, filed on Mar. 5, 1998, now Pat. No. 6,099,497.

(51) Int. Cl.
*A61M 29/00* (2006.01)
*A61F 2/06* (2006.01)

(52) U.S. Cl. ............... 604/96.01; 623/1.11; 606/108

(58) Field of Classification Search ............. 604/96.01, 604/101.01, 102.01, 102.02, 103.09; 606/108; 623/1.11

See application file for complete search history.

(56) References Cited

U.S. PATENT DOCUMENTS

| 4,730,616 | A | 3/1988 | Frisbie et al. |
| 4,896,670 | A | 1/1990 | Crittenden |
| 4,994,071 | A | 2/1991 | MacGregor |
| 5,143,093 | A | 9/1992 | Sahota |
| 5,192,297 | A | 3/1993 | Hull |
| 5,219,355 | A | 6/1993 | Parodi et al. |
| 5,316,023 | A | 5/1994 | Palmaz et al. |
| 5,320,605 | A | 6/1994 | Sahota |
| 5,413,581 | A | 5/1995 | Goy |
| 5,505,702 | A | 4/1996 | Arney |
| 5,591,228 | A | 1/1997 | Edoga |
| 5,607,444 | A | 3/1997 | Lam |
| 5,609,627 | A | 3/1997 | Goicoechea et al. |
| 5,613,980 | A * | 3/1997 | Chauhan .................. 606/194 |
| 5,617,878 | A | 4/1997 | Taheri |
| 5,626,600 | A | 5/1997 | Horzewski et al. |
| 5,632,762 | A | 5/1997 | Myler |
| 5,632,763 | A | 5/1997 | Glastra |
| 5,632,772 | A | 5/1997 | Alcime et al. |
| 5,639,278 | A | 6/1997 | Dereume et al. |
| 5,643,340 | A | 7/1997 | Nunokawa |

(Continued)

FOREIGN PATENT DOCUMENTS

EP     0479730 B1     4/1992

(Continued)

*Primary Examiner* — Vy Q Bui

(74) *Attorney, Agent, or Firm* — Vidas, Arrett & Steinkraus, P.A.

(57) ABSTRACT

The present invention provides a dilatation and stent delivery device which tracks over two guidewires. One guidewire is disposed in each branch vessel of a bifurcation. The present invention provides a dilatation and stent delivery device which enables efficient and accurate stent deployment and dilatation of bifurcation lesions.

5 Claims, 13 Drawing Sheets

U.S. PATENT DOCUMENTS

| | | | |
|---|---|---|---|
| 5,669,924 | A | 9/1997 | Shaknovich |
| 5,720,735 | A | 2/1998 | Dorros |
| 5,749,825 | A | 5/1998 | Fischell et al. |
| 5,749,890 | A | 5/1998 | Shaknovich |
| 5,755,734 | A | 5/1998 | Richter et al. |
| 5,755,735 | A | 5/1998 | Richter et al. |
| 5,755,770 | A | 5/1998 | Ravenscroft |
| 5,755,771 | A | 5/1998 | Penn et al. |
| 5,755,772 | A | 5/1998 | Evans et al. |
| 5,755,773 | A | 5/1998 | Evans et al. |
| 5,755,778 | A | 5/1998 | Kleshinski |
| 5,776,101 | A | 7/1998 | Goy |
| 5,782,906 | A | 7/1998 | Marshall et al. |
| 5,833,650 | A | 11/1998 | Imran |
| 5,846,246 | A | 12/1998 | Dirks et al. |
| 5,882,236 | A | 3/1999 | Ozawa et al. |
| 5,980,484 | A | 11/1999 | Ressemann et al. |
| 6,096,073 | A * | 8/2000 | Webster et al. .............. 623/1.16 |
| 6,099,497 | A | 8/2000 | Adams et al. |
| 6,117,104 | A | 9/2000 | Fitz |
| 6,120,477 | A | 9/2000 | Campbell et al. |
| 6,165,195 | A | 12/2000 | Wilson et al. |
| 6,210,429 | B1 | 4/2001 | Vardi et al. |
| 6,290,673 | B1 | 9/2001 | Shanley |
| 6,309,379 | B1 | 10/2001 | Willard et al. |
| 6,361,544 | B1 | 3/2002 | Wilson et al. |
| 6,379,372 | B1 | 4/2002 | Dehdashtian et al. |
| 6,494,875 | B1 | 12/2002 | Mauch |
| 6,514,281 | B1 | 2/2003 | Blaeser et al. |
| 6,520,988 | B1 | 2/2003 | Colombo et al. |
| 6,579,312 | B2 | 6/2003 | Wilson et al. |
| 6,582,394 | B1 | 6/2003 | Reiss et al. |
| 6,656,213 | B2 | 12/2003 | Solem |
| 6,663,665 | B2 | 12/2003 | Shaolian et al. |
| 6,669,718 | B2 | 12/2003 | Besselink |
| 6,676,691 | B1 | 1/2004 | Hosny |
| 2002/0193873 | A1 | 12/2002 | Brucker et al. |
| 2003/0125791 | A1 | 7/2003 | Sequin et al. |
| 2003/0139796 | A1 | 7/2003 | Sequin et al. |
| 2003/0181923 | A1 | 9/2003 | Vardi |

FOREIGN PATENT DOCUMENTS

| | | |
|---|---|---|
| EP | 0686379 A2 | 12/1995 |
| WO | 95/21592 A1 | 8/1995 |
| WO | 96/34580 A1 | 11/1996 |
| WO | 96/41592 A1 | 12/1996 |
| WO | 97/07752 A1 | 3/1997 |
| WO | 97/15346 A1 | 5/1997 |
| WO | 97/41803 A1 | 11/1997 |
| WO | 98/19628 A1 | 5/1998 |

* cited by examiner

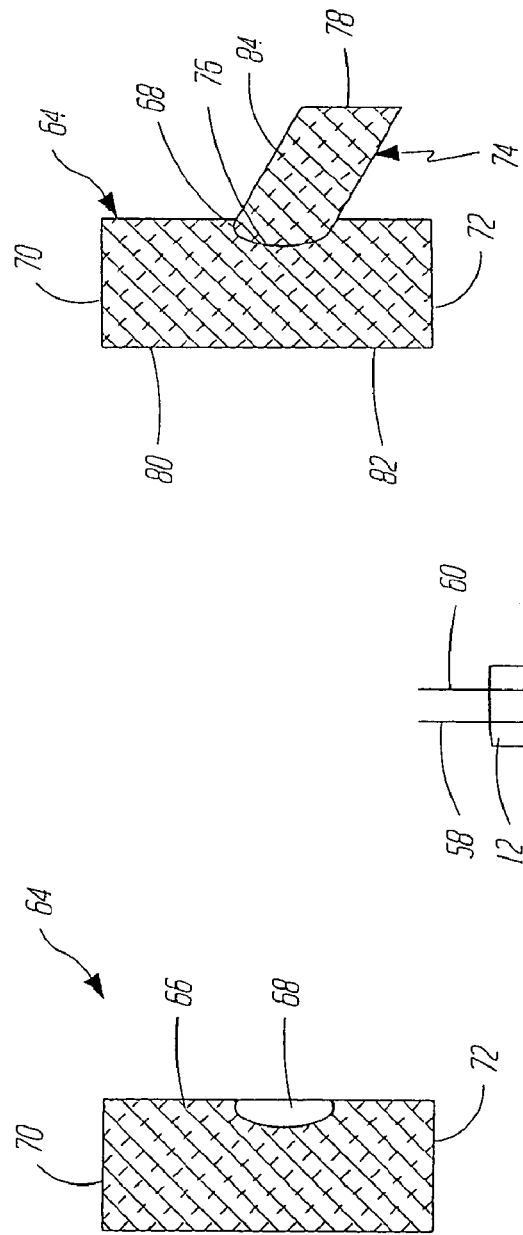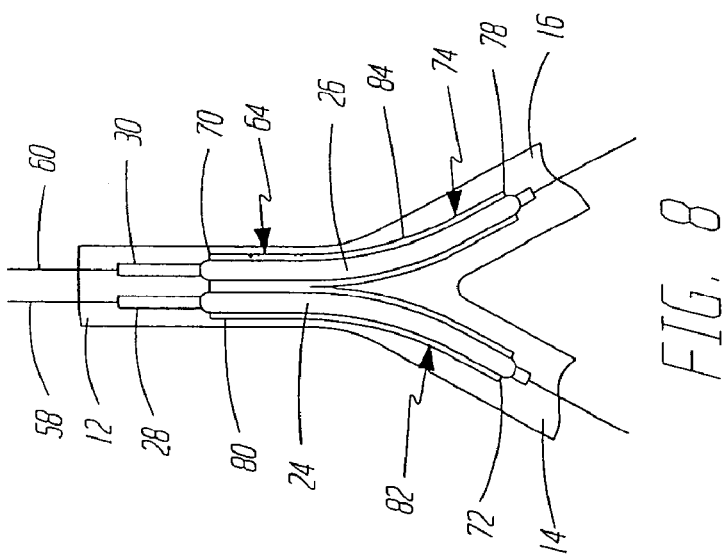

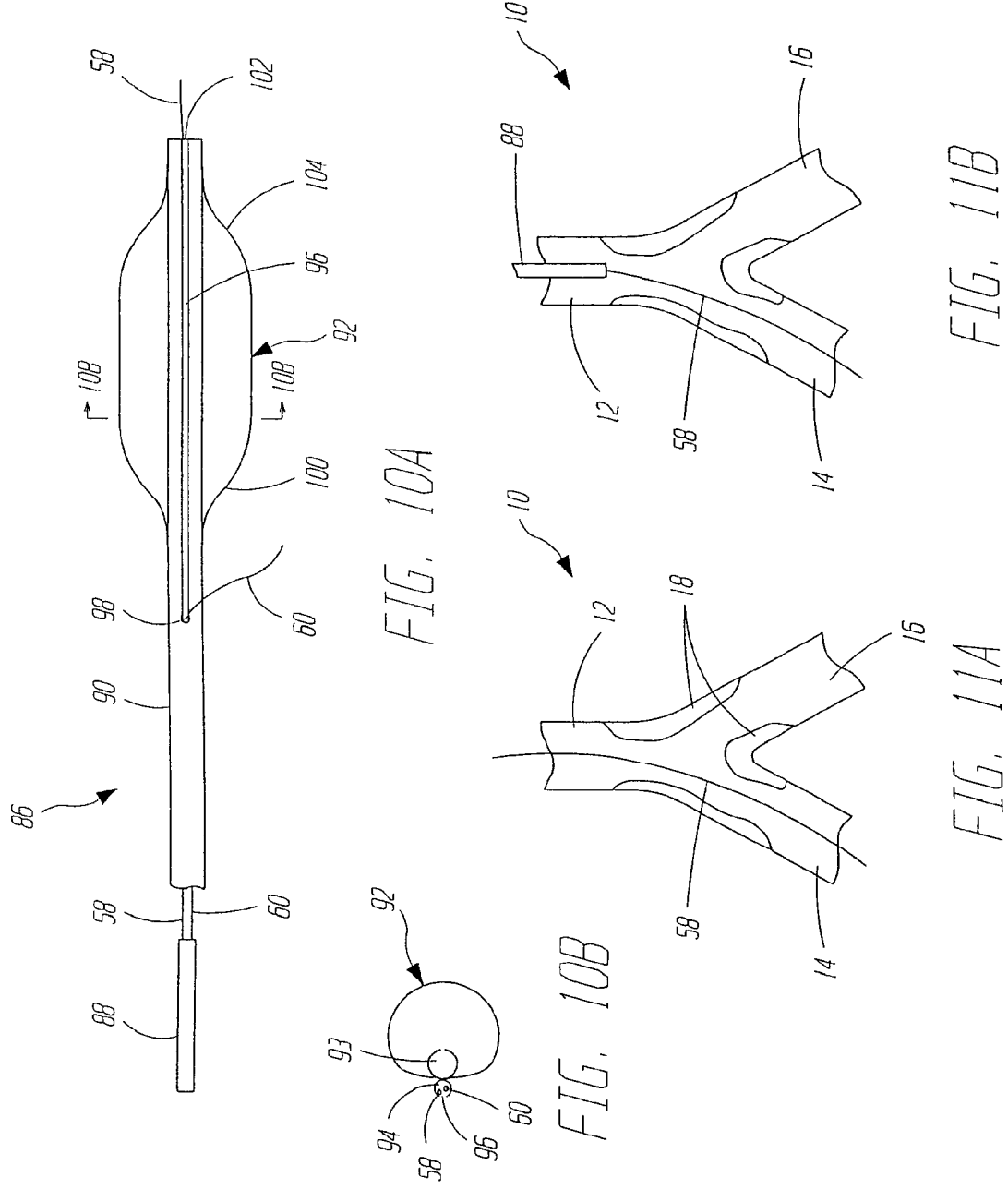

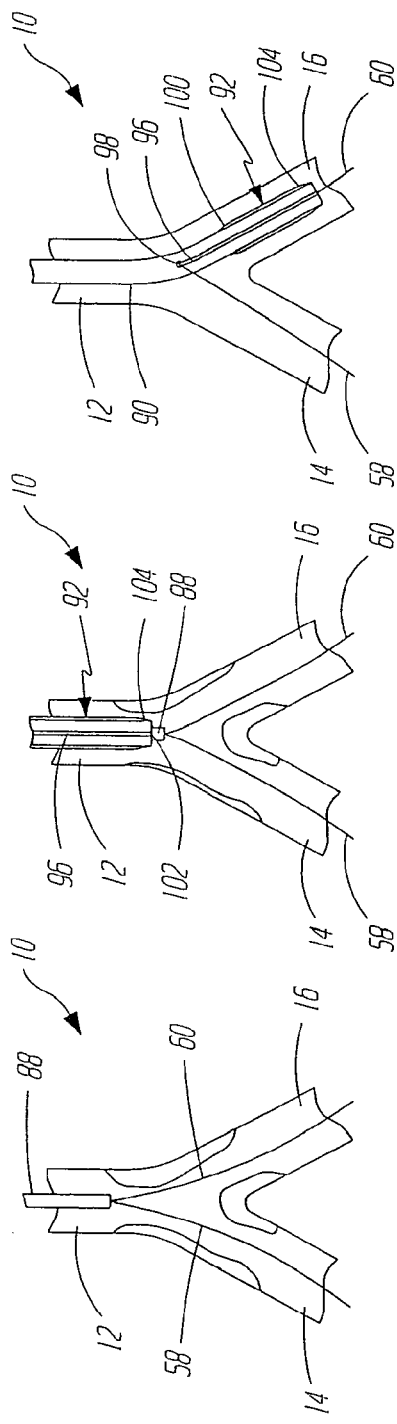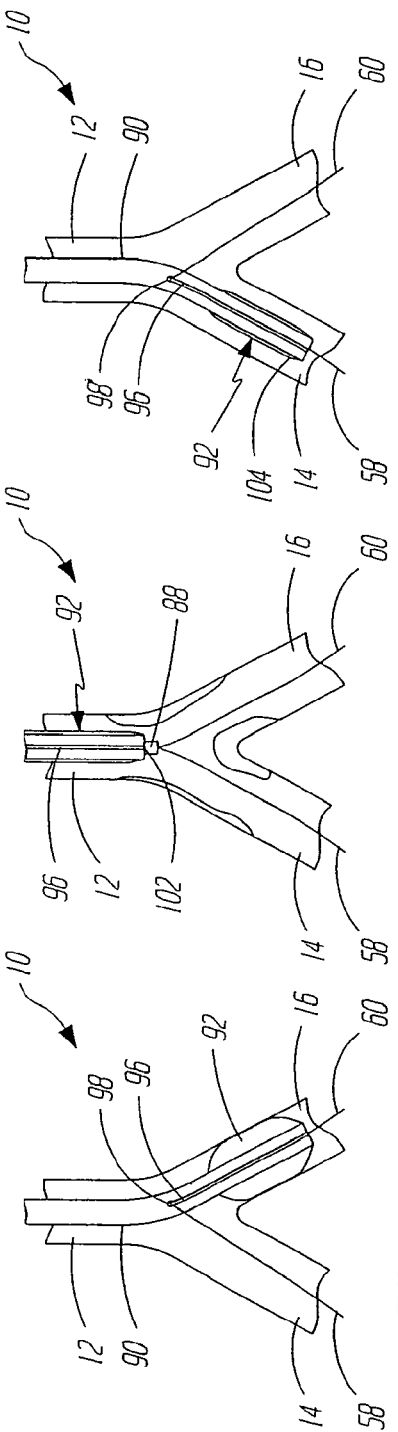

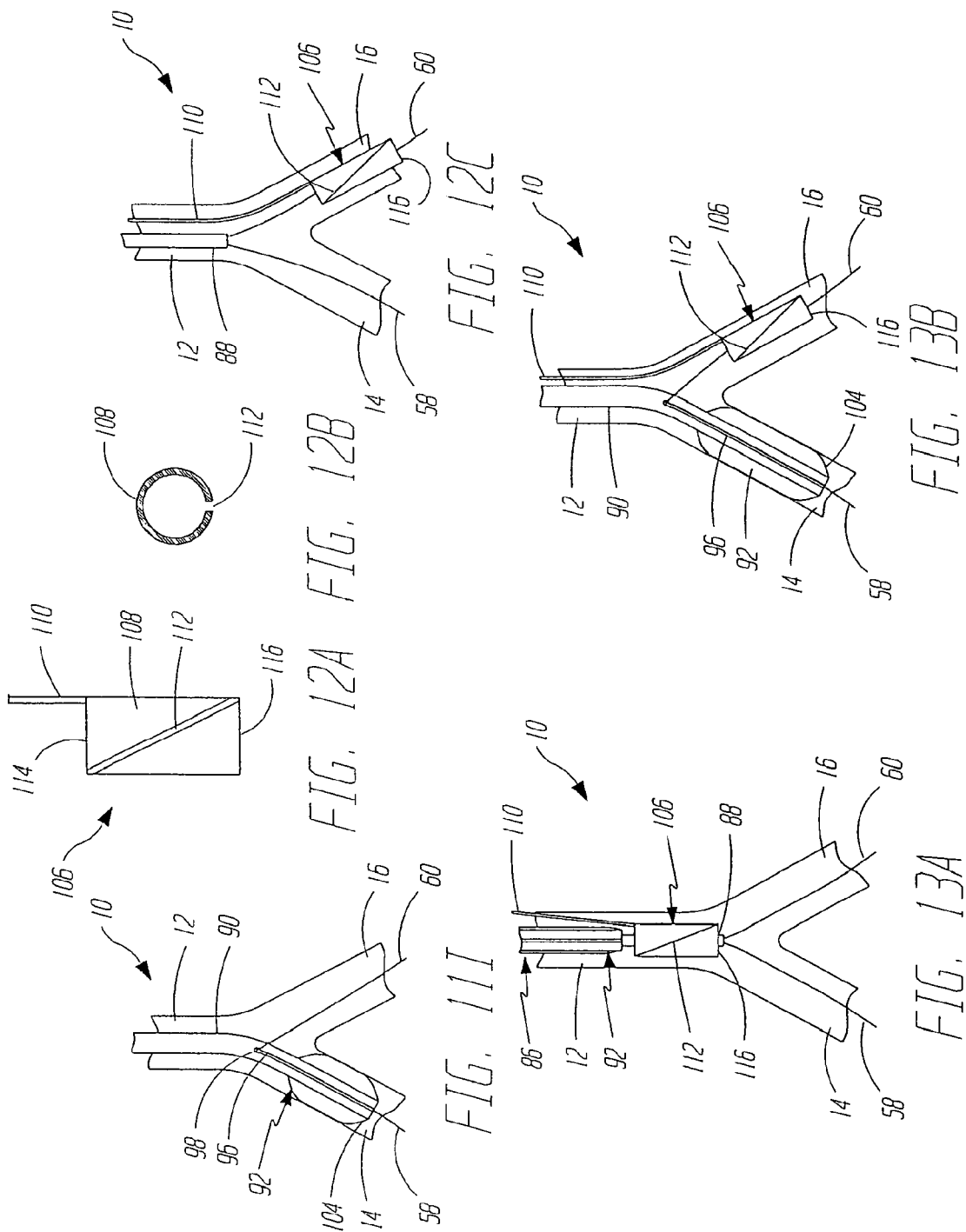

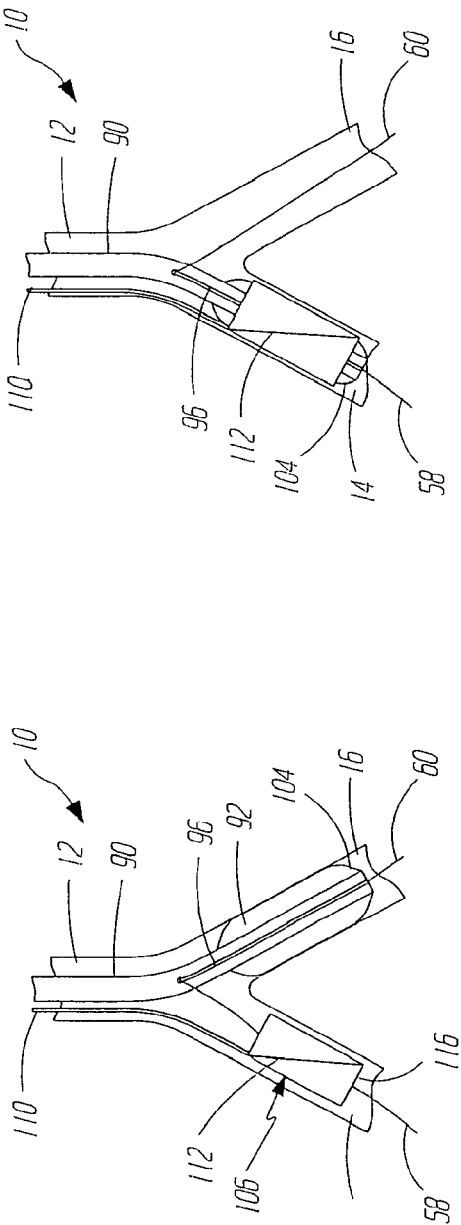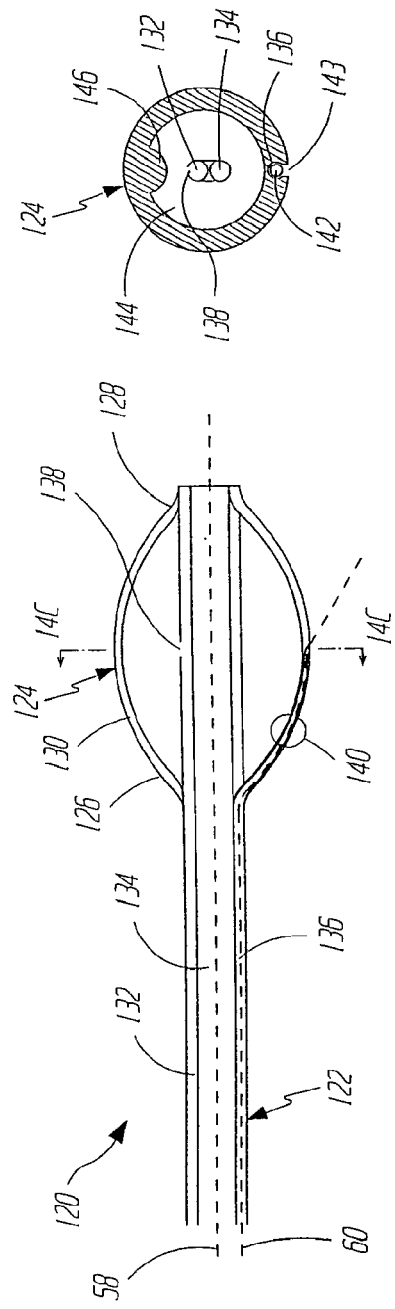

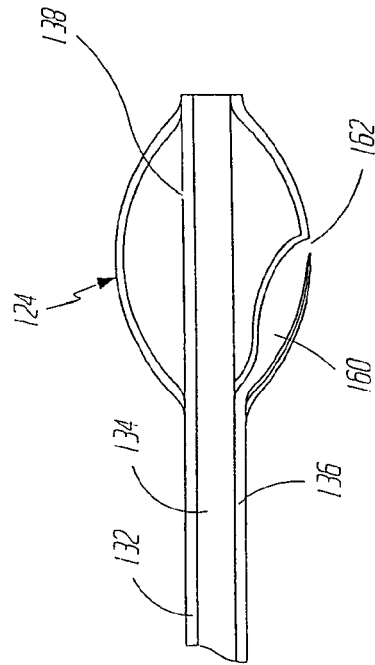
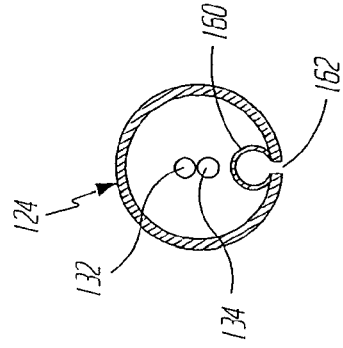
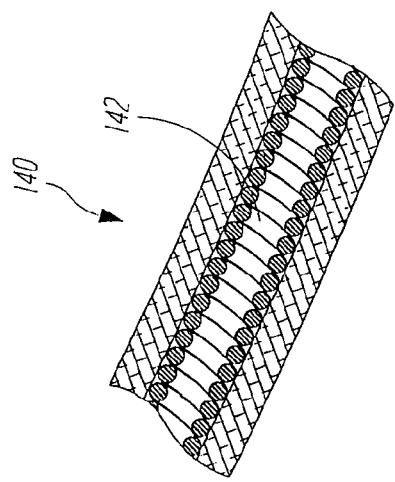
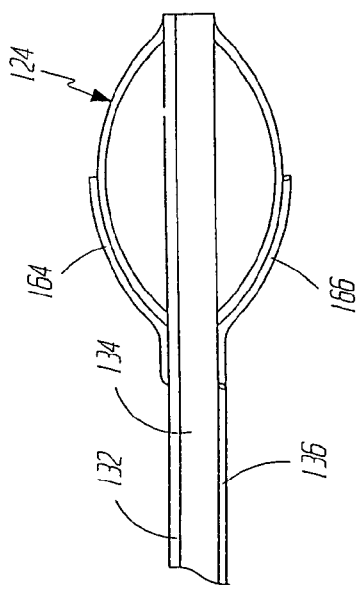

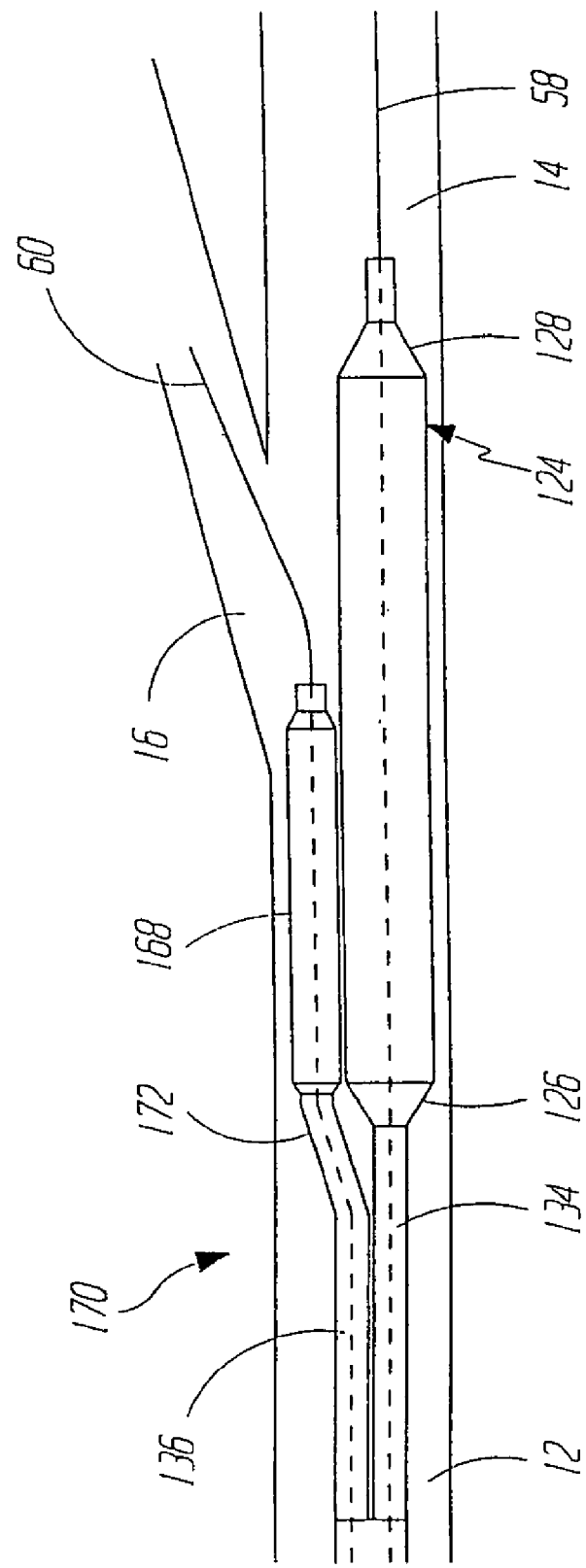

DILATION AND STENT DELIVERY SYSTEM FOR BIFURCATION LESIONS

CROSS-REFERENCE TO RELATED APPLICATIONS

This application is a Continuation application claiming priority from U.S. patent application Ser. No. 10/768,561, filed Jan. 30, 2004 now U.S. Pat. No. 7,445,610, which is a Continuation application claiming priority from U.S. patent application Ser. No. 09/590,885, filed Jun. 9, 2000 and now abandoned, which is a Continuation application claiming priority from U.S. patent application Ser. No. 09/035,642, filed Mar. 5, 1998 and now U.S. Pat. No. 6,099,497, the entire contents of each being expressly incorporated herein by reference.

BACKGROUND OF THE INVENTION

The present invention relates to a system for treating vascular disease. More specifically, the present invention relates to a system for treating a lesion at a bifurcation in the vasculature.

Vascular disease currently represents a prevalent medical condition. Typical vascular disease involves the development of a stenosis in the vasculature. The particular vessel containing the stenosis can be completely blocked (or occluded) or it can simply be narrowed (or restricted). In either case, restriction of the vessel caused by the stenotic lesion results in many well known problems caused by the reduction or cessation of blood circulation through the restricted vessel.

A bifurcation is an area of the vasculature where a first (or parent) vessel is bifurcated into two or more branch vessels. It is not uncommon for stenotic lesions to form in such bifurcations. The stenotic lesions can affect only one of the vessels (i.e., either of the branch vessels or the parent vessel), two of the vessels, or all branch vessels.

A number of different procedures have been developed to treat a stenotic lesion (stenosis) in the vasculature. The first is to deform the stenosis to reduce the restriction within the lumen of the blood vessel. This type of deformation (or dilatation) is typically performed using balloon angioplasty.

However, when the lesion is formed in a bifurcation, conventional balloon angioplasty can be somewhat cumbersome. In some cases, two separate guidewires are used. However, where only one guidewire is used, the guidewire is first introduced into one of the branch vessels of the bifurcation. The dilatation balloon is then advanced over the guidewire so the distal end of the dilatation balloon is in the branch vessel. The balloon is then inflated a number of times, in a known manner, to accomplish dilatation.

The balloon is then withdrawn proximal of the bifurcation. The guidewire is then withdrawn and manipulated into the other branch vessel of the bifurcation. The balloon is then advanced over the guidewire, again, and inflated to dilate the second branch vessel.

Not only is this process somewhat cumbersome, other problems result as well. For example, when the angle between the branch vessels in the bifurcation is fairly small, inflation of the dilatation balloon in one branch vessel can cause the ostium of the other branch vessel to collapse. This results in ineffective dilatation by restricting flow to the other branch vessel.

Further, locating both branch vessels can be quite difficult. For example, once the first branch vessel is located under conventional visualization techniques (such as with the use of contrast medium), that vessel is dilated. After withdrawing both the guidewire and the dilatation catheter proximal of the bifurcation, the physician must then attempt to locate the second branch vessel. This can require the introduction of other devices into the vasculature and the region of the bifurcation. This can be somewhat cumbersome.

Vascular stents are also currently well known, and are deployed as another technique for treating vascular lesions. Vascular stents typically involve a tubular stent which is movable from a collapsed, low profile, delivery position to an expanded, deployed position. The stent is typically delivered using a stent delivery device, such as a stent delivery catheter. In one common technique, the stent is crimped down to its delivery position over an expandable element, such as a stent deployment balloon. The stent is then advanced (using the catheter attached to the stent deployment balloon) to the lesion site under any suitable, commonly known visualization technique. The balloon is then expanded to drive the stent from its delivery position to its deployed position in which the outer periphery of the stent frictionally engages the inner periphery of the lumen. In some instances, the lumen is predilated using a conventional dilatation catheter, and then the stent is deployed to maintain the vessel in an unoccluded, and unrestricted position.

While there have recently been considerable advances in stent design and stent deployment techniques, there is currently no adequate method of treating bifurcation lesions, particularly where both downstream branch vessels are affected by the lesion. Current techniques of dealing with such lesions typically require the deployment of a slotted tube stent across the bifurcation. However, this compromises the ostium of the unstented branch.

Further, once the first stent is deployed, the treating physician may then advance a dilatation balloon between the struts of the stent already deployed in order to dilate the second branch vessel. The physician must then attempt to maneuver a second stent through the struts of the stent already deployed, into the second branch vessel for deployment. This presents significant difficulties. For example, dilating between the struts of the stent already deployed tends to distort that stent. Further, deploying the second stent through the struts of the first stent is not only difficult, but it can also distort the first stent.

SUMMARY OF THE INVENTION

The present invention provides a dilatation and stent delivery device which tracks over two guidewires. One guidewire is disposed in each branch vessel of a bifurcation. The present invention provides a dilatation and stent delivery device which enables efficient and accurate stent deployment and dilatation of bifurcation lesions.

BRIEF DESCRIPTION OF THE DRAWINGS

FIGS. 7A and 7B illustrate a bifurcated stent in accordance with one aspect of the present invention.

FIGS. 8 and 9 illustrate deployment of the stent shown in FIGS. 7A and 7B.

FIGS. 10A-10C show another dilatation and stent deployment device in accordance with one aspect of the present invention.

FIGS. 11A-11I illustrate use of the device shown in FIGS. 10A-10B for dilatation of a bifurcation lesion.

FIGS. 12A-12C illustrate a perfusion tube in accordance with another aspect of the present invention.

FIGS. 13A-13D illustrate use of the perfusion tube illustrated in FIGS. 12A-12C.

FIGS. 14A-14D illustrate another dilatation and stent deployment device in accordance with one aspect of the present invention.

FIGS. 15A-15B illustrate another embodiment of the dilatation stent delivery device shown in FIGS. 14A-14D FIGS. 16-18 illustrate other embodiments of a dilatation and stent delivery device in accordance with other aspects of the present invention.

DETAILED DESCRIPTION OF THE PREFERRED EMBODIMENTS

Figure 1:
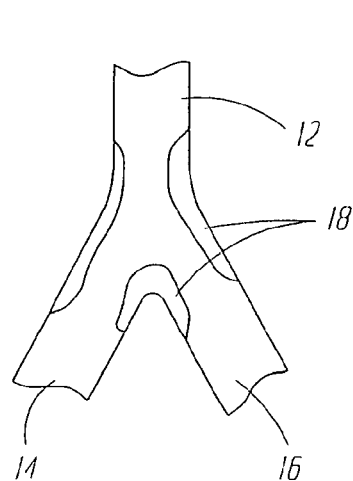
FIG. 1 illustrates a typical bifurcation lesion.

FIG. 1 illustrates a bifurcation 10 which includes parent vessel 12, first branch vessel 14 and second branch vessel 16. FIG. 1 also illustrates that a bifurcation lesion 18 has developed in bifurcation 10. Lesion 18 illustrates one common bifurcation lesion in that it extends up into parent vessel 12 and down into both branch vessels 14 and 16.

Figure 2B:
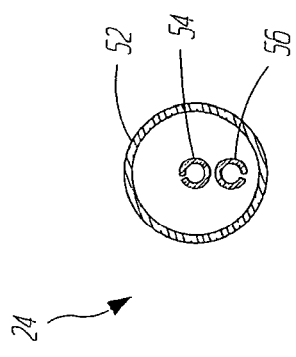
FIGS. 2A and 2B illustrate a dilatation and stent deployment device in accordance with one aspect of the present invention.
Figure 2A:
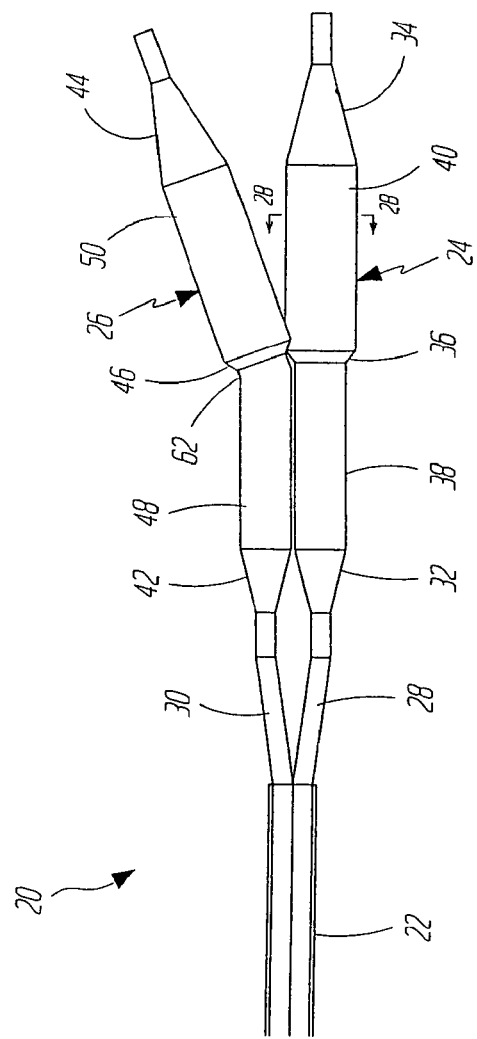

FIGS. 2A and 2B illustrate a dilatation and stent deployment device 20 in accordance with one aspect of the present invention. Device 20 includes a first sheath 22, and a pair of dilatation balloons 24 and 26. Each dilatation balloon 24 and 26 is coupled to a balloon catheter 28 and 30, respectively, both of which fit within sheath 22. It should also be noted that sheath 22 can be a separate member preferably fixedly disposed about balloon catheters 28 and 30 or can be a dual lumen extrusion which forms part of catheters 28 and 30. In a preferred embodiment, balloons 24 and 26 are similar in construction. Balloon 24 preferably includes proximal end 32 and distal end 34 with an intermediate portion 36 therebetween. The region of balloon 24 between proximal end 32 and intermediate portion 36 preferably forms a smaller diameter (or narrower) balloon segment 38. The region of balloon 24 between intermediate portion 36 and distal end 34 preferably forms a larger diameter balloon segment 40.

Similarly, balloon 26 preferably has a proximal end 42, a distal end 44, and an intermediate portion 46 therebetween. The region between proximal end 42 and intermediate region 46 preferably forms a smaller diameter (or narrower) balloon segment 48, while the portion of balloon between intermediate region 46 and distal end 44 preferably forms a larger diameter balloon segment 50.

As will be described in greater detail later in the specification, smaller diameter balloon segments 38 and 48 are preferably formed to reside adjacent one another in parent vessel 12, while larger diameter balloon segments 40 and 50 preferably reside in branch vessels 14 and 16, during dilatation and stent deployment.

In one preferred embodiment, intermediate section 46 of balloon 26 is simply a necked down diameter reduction area which smoothly transitions the outer diameter of balloon 26 from the larger diameter of balloon segment 50 to the smaller diameter of balloon segment 48. Similarly, intermediate section 36 is a necked down portion which transitions the outer diameter of balloon 24 from the large diameter balloon segment 40 to the smaller diameter balloon segment 38. Further, intermediate section 46 preferably (and optionally) includes a preformed bend section 62. Preformed bend section 62 is preferably formed such that distal end 44 of balloon 26 extends away from distal end 34 of balloon 24 at any desired angle .alpha. In one preferred embodiment, .alpha. is in a range of approximately 30.degree.-70.degree., while in another preferred embodiment, .alpha. is in a range of approximately 45.degree.-60.degree. In any case, upon inflation of balloon 26, preformed bend region 62 causes balloon 26 to deform in the shape shown in FIGS. 2A and 6 such that it can more easily find branch vessel 16, and track guidewire 60 into branch vessel 16.

FIG. 2B is a cross-sectional end view of balloon 24 taken along section lines 2B-2B in FIG. 2A further illustrating the construction of balloons 24 and 26. Both balloons 24 and 26 are similar with respect to the view shown in FIG. 2B. Therefore, only balloon 24 will be described, for the sake of clarity. Balloon 24 preferably includes an outer wall 52 of expandable balloon material. Balloon 24 also preferably includes an inner guidewire lumen 54, and an inflation lumen 56. In one preferred embodiment, guidewire lumen 54 and inflation lumen 56 are coaxially aligned with guidewire lumen 54 disposed within inflation lumen 56. Inflation lumen 56 terminates at a proximal region of balloon 24 while guidewire lumen 54 extends through balloon 24 and is bonded to the distal end thereof. In one preferred embodiment, the length from the distal tip of balloon 24 to the distal end of sheath 22 measures approximately 25 cm. Both guidewire lumen 54 and inflation lumen 56 extend from balloon 24 all the way to a proximal end of sheath 22, which preferably resides outside the body during dilatation and stent delivery. However, in another preferred embodiment, only inflation lumen 56 extends all the way to the proximal end of sheath 22, while guidewire lumen 54 is of a monorail construction which has a proximal ostium proximal of balloon 24, and has a distal ostium in the region of the distal tip 34 of balloon 24. In yet another embodiment, the inflation lumens of both balloons 24 and 26 are combined proximal of the balloons to accommodate simultaneous inflation of balloons 24 and 26.

In any case, both balloons can also have an inflation lumen and a guidewire lumen, so they are suitable for independent inflation, and for tracking of separate guidewires. It should also be noted that, in the preferred embodiment, when balloons 24 and 26 are in the deflated, insertion position, they obtain a low enough profile to both fit within a guide catheter (not shown).

Figure 3:
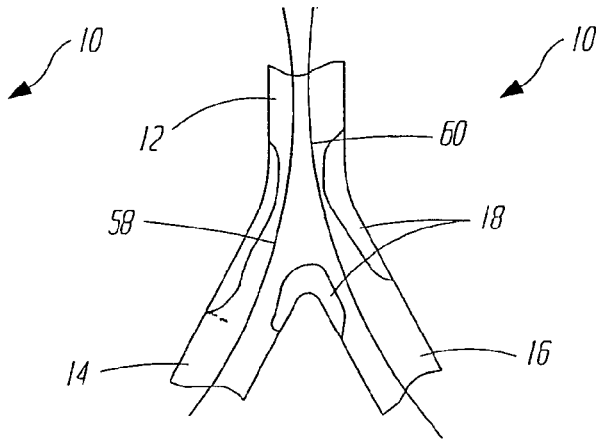
FIGS. 3-6 illustrate dilatation of a bifurcation lesion using the device shown in FIG. 2.
Figure 4:
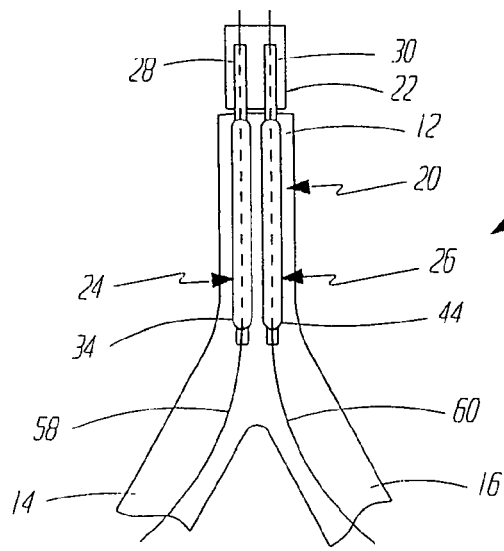

FIGS. 3-6 illustrate dilatation of bifurcation 10 in accordance with one aspect of the present invention. FIG. 3 illustrates that, in a first step, two guidewires 58 and 60 are first introduced into the vasculature (such as through a femoral artery and a guide catheter) and are advanced to bifurcation 10. Guidewire 58 is manipulated such that it is advanced down branch vessel 14, while guidewire 60 is manipulated to be advanced down branch vessel 16.

Once guidewires 58 and 60 are positioned as shown in FIG. 3, device 20 is then advanced over guidewires 58 and 60. This is illustrated in greater detail in FIG. 4. Device 20 is preferably preloaded, or backloaded, onto guidewires 58 and 60 with balloons 24 and 26 in the deflated position. Thus, guidewire 58 extends through the guidewire lumen in balloon 24, while guidewire 60 extends through the guidewire lumen in balloon 26. Sheath 22 and balloons 24 and 26 are then advanced over guidewires 58 and 60 to bifurcation 10. The insertion of device 20 is preferably observed by the treating physician under any suitable visualization technique, such as through the introduction of contrast medium, or fluoroscopy, or the like.

Figure 5:
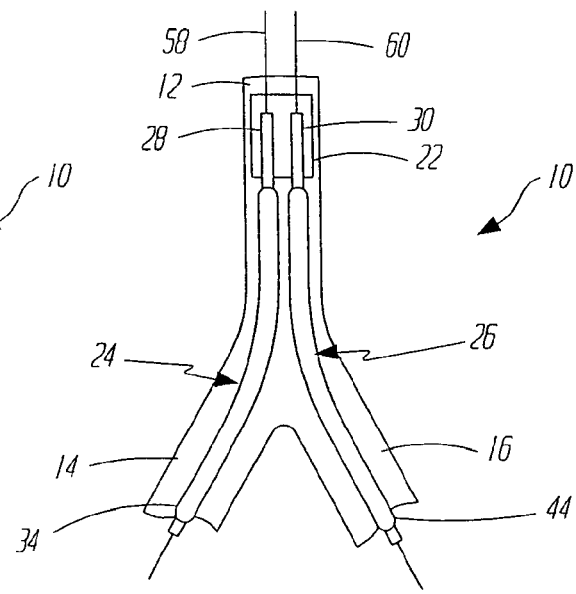

FIG. 5 illustrates that balloons 24 and 26 are then advanced over guidewires 58 and 60 until the distal tips 34 and 44 of balloons 24 and 26 reside at a desirable location within branch vessels 14 and 16, respectively. In one preferred embodiment, balloons 58 and 60, and their corresponding catheters 28 and 30, are movable independently of one another. However, in another preferred embodiment, they are fixed relative to one another and sheath 22 and move as a unitary member. Balloons 24 and 26 can be positioned as desired by the treating physician, in order to accomplish optimal dilatation, based upon the size and location of bifurcation 10, and the size of lesion 18.

Figure 6:
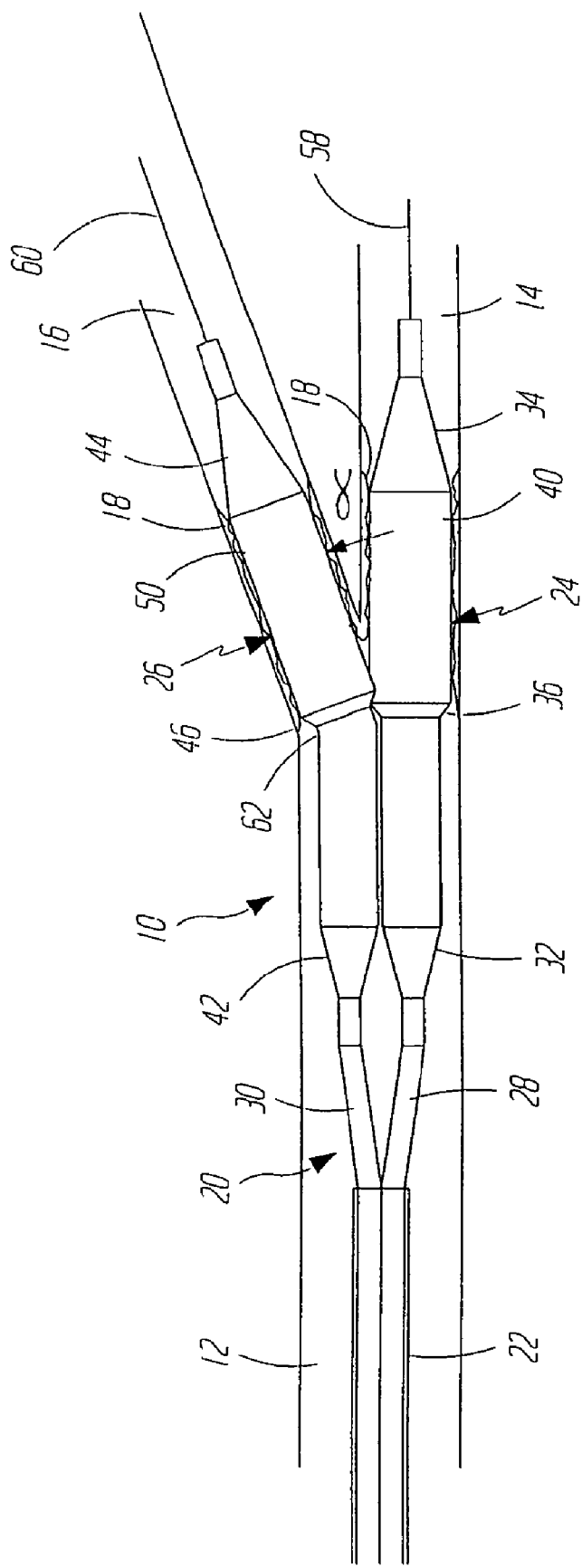

Once balloons 24 and 26 are positioned as shown in FIG. 5, they are inflated to accomplish dilatation of bifurcation 10. This is illustrated in FIG. 6. FIG. 6 also illustrates that the two smaller diameter balloon segments 38 and 48 combine to provide dilatation force in parent vessel 12 of bifurcation 10. In addition, larger diameter balloon segments 40 and 50 extend within branch vessels 14 and 16, respectively, to dilate lesion 18 in those vessels.

Once placed in the position shown in FIG. 6, and inflated, balloons 24 and 26 can be deflated and re-inflated any desired number of times, to accomplish optimal dilatation. Once dilatation has been accomplished, balloons 24 and 26 are preferably deflated, and withdrawn proximally over guidewires 58 and 60 and removed from the vasculature.

In accordance with one aspect of the present invention, after the dilatation illustrated by FIG. 6, it may be desirable to deploy a stent in bifurcation 10. FIGS. 7A and 7B illustrate a stent which can be deployed by device 20 in bifurcation 10. FIG. 7A illustrates that the bifurcation stent preferably includes a first stent portion 64. Stent portion 64 can be any suitable, and commercially available stent, such a Palmaz-Schatz stent or an NIR stent. Stent 64 preferably includes a tubular structural wall 66. Wall 66 preferably has an aperture 68 formed therein, near a midregion of stent 64, between a first end 70 and a second end 72 thereof. FIG. 7B illustrates that the bifurcated stent also preferably includes a second stent portion 74. Second stent portion 74 preferably has a first end 76 and a second end 78, wherein the first end 76 is cut at an angle relative to the longitudinal axis of stent 74. First end 76 is preferably coupled to stent 64 about aperture 68, thus forming a bifurcated stent having a first portion 80 which is configured to reside in the parent vessel, and two depending portions 82 and 84 which are configured to be received within branch vessels 14 and 16, respectively.

In another preferred embodiment, the stent is manufactured as one integral stent having a conformation with a main section and two depending leg sections.

Figure 9:
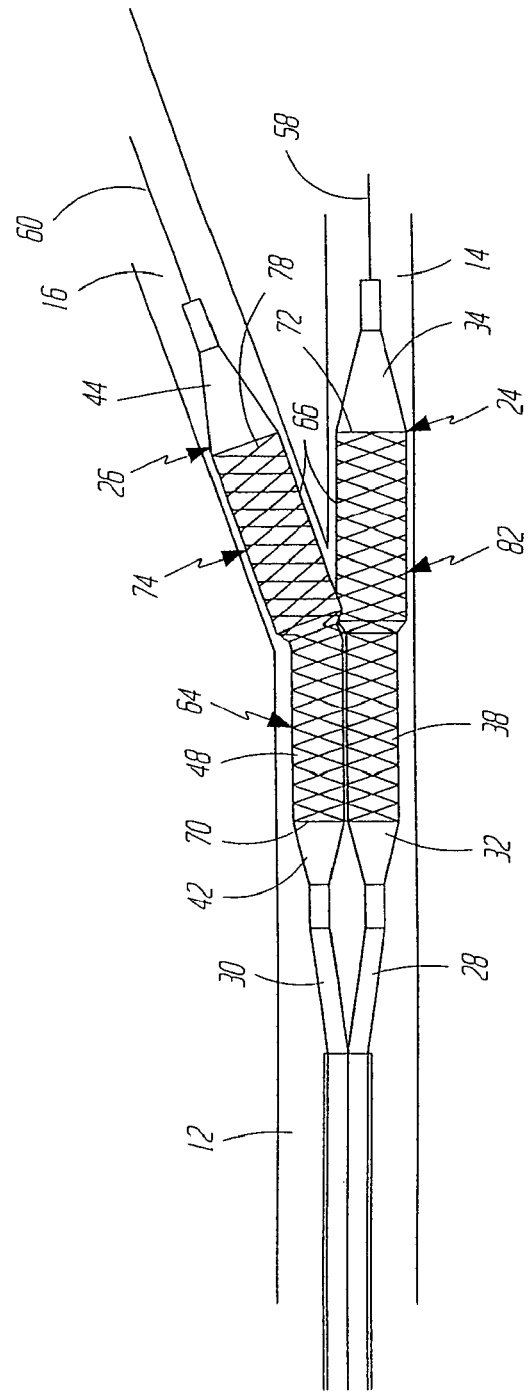

In order to deploy the bifurcated stent illustrated in FIG. 7B, the stent is first preloaded onto device 20 (as shown in FIGS. 8 and 9) such that first portion 80 is disposed over the smaller diameter balloon segments 38 and 48 of balloons 24 and 26, respectively. Also, depending portions 82 and 84 are preferably disposed over the larger diameter balloon segments 40 and 50. Of course, the bifurcated stent is preferably loaded onto device 20 while the balloons 24 and 26 are in the deflated position and the stent is crimped down over balloons 24 and 26 for delivery.

Next, balloons 24 and 26, (either before or after the bifurcated stent is disposed thereon) are backloaded onto guidewires 58 and 60. Device 20 is then advanced through the vasculature (in the same manner as indicated above with respect to FIGS. 3-5) until balloons 24 and 26, with a bifurcated stent mounted thereon, are disposed in bifurcation 10 in the position shown in FIG. 8. Balloons 24 and 26 are then inflated, as shown in FIG. 9. This drives the bifurcated stent from a collapsed, insertion position to a radially expanded, deployed position in which the outer periphery of the tubular structure 66 frictionally engages the inner periphery of the lumen walls of both branch vessels 14 and 16, and of parent vessel 12.

Thus, it can be seen that device 20 provides significant advantages over prior bifurcation dilatation and stent deployment techniques. For example, device 20 is capable of dilating both branch vessels 14 and 16 at the same time. Similarly, device 20 is capable of deploying a stent in both branch vessels at the same time. This significantly reduces the likelihood that either of the branch vessels 14 or 16 will collapse during dilatation and stent deployment. Further, both dilatation and stent deployment can be accomplished without removing either of the guidewires 58 or 60, or without repositioning either of the guidewires. Rather, the guidewires simply need to be placed at the appropriate positions within branch vessels 14 and 16, and left throughout both dilatation and stent deployment.

Figure 10C:
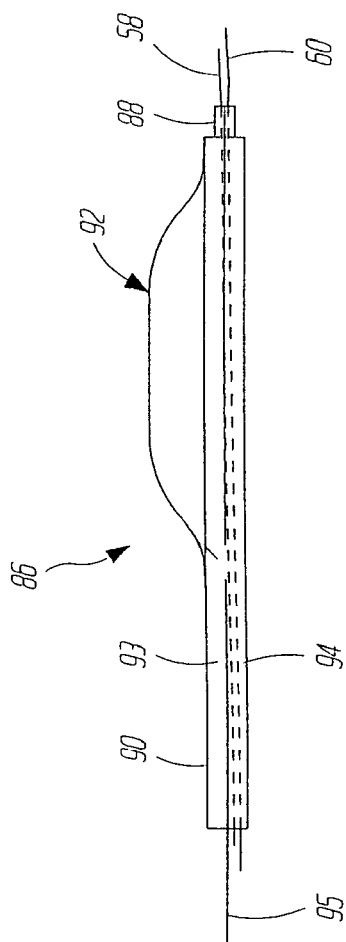

FIGS. 10A-10C illustrate another bifurcation dilatation device 86 in accordance with another aspect of the present invention. FIG. 10B is a cross-sectional view taken along section lines 10B-10B in FIG. 10A and FIG. 10C is a view rotated 90.degree. about the longitudinal axis relative to the view shown in FIG. 10A. Device 86 includes guidewire sheath 88, catheter 90, and balloon 92. Sheath 88 is preferably a separate member from catheter 90 and balloon 92. FIG. 10A also shows both guidewires 58 and 60. Guidewires 58 and 60 are preferably approximately 0.010 inches in diameter, but can have any suitable guidewire dimensions. Guidewire sheath 88 is preferably simply a sheath (typically polyethylene) which is disposed about guidewires 58 and 60, and is sized to be advanced over guidewires 58 and 60 through the vasculature, to bifurcation 10, preferably through a guide catheter (not shown). Sheath 88 can also be implemented as a dual lumen sheath wherein a guidewire is received in each lumen. This helps prevent the guidewires from entangling. Balloon 92 preferably includes a proximal end 100 and a distal end 104 and is eccentrically located on shaft 90. Distal end 104 is preferably disposed just proximal of the distal tip of shaft 90. Balloon 92 and the lumens 93 and 94 can be formed by using a triple lumen extrusion process. Alternatively, the lumens can be formed by discrete processing steps, such as inserting a lumen tube through balloon 92 and then bonding or welding the lumen tube to the balloon, or shaft 90, at appropriate locations.

In an embodiment in which shaft 92 is an over-the-wire shaft, it is preferably formed of a suitable polymer material. However, shaft 92 can also extend proximally to a stainless steel hypotube shaft (not shown) and be bonded to the stainless steel hypotube shaft at a desirable location. It may also be desirable to have a stainless steel extension, or support shaft 95, extending from the hypotube shaft to a region proximate balloon 92, to provide rigidity to enhance pushability of shaft 90 and balloon 92.

Shaft 90 also preferably includes an inflation lumen 93 (shown in FIG. 10B), as well as guidewire sheath lumen 94. Inflation lumen 93 has an opening 97 which communicates with the interior of balloon 92. Lumen 93 extends proximally along shaft 90, all the way to the proximal end of shaft 90 which resides outside the body during dilatation and/or stent deployment. Guidewire sheath lumen 94, on the other hand, can extend all the way to the proximal end of shaft 90, or can have a proximal ostium which is disposed just proximal of the proximal end 100 of balloon 92, and also proximal of the proximal end 98 of slit 96 (described below)

In one preferred embodiment, shaft 90 includes slit 96 which has a proximal end 98, disposed just proximal of proximal end 100 of balloon 92, and a distal end 102 which is coterminous with the distal tip of balloon 92. In one embodiment, slit 96 is simply a cut or separation made in the wall of shaft 90. Preferably, the distal end of slit 96 has a v-cut lead in and the proximal end has a relief hole to inhibit tearing.

As will be described in greater detail with respect to FIGS. 11A-11I, single balloon 92 and device 86 can be used to dilate both branch vessels 14 and 16 of bifurcation 10 by alternatively switching from following one guidewire 58, to following the other guidewire 60, without removal of device 86 from the vessel. Briefly, this is done by first advancing balloon 92 along guidewire 58, while allowing guidewire 60 to slip through slit 96 as balloon 92 enters the first branch vessel 14. Then, balloon 92 is withdrawn such that both guidewires 58 and 60 are again within guidewire lumen 94. Balloon 92 is then rotated and advanced along guidewire 60, allowing guidewire 58 to exit guidewire lumen 94 through slit 96. This allows balloon 92 to be advanced along guidewire 60 into the other branch vessel 16 for dilatation of that branch vessel.

More specifically, FIG. 11A illustrates a first step in dilating bifurcation 10 with device 86. Guidewire 58 is first advanced to bifurcation 10, and the lesion in branch vessel 14 is crossed with guidewire 58. Then, as shown in FIG. 11B, guidewire sheath 88 is advanced over guidewire 58 such that its distal end is disposed just proximal of bifurcation 10. Guidewire 60 is then advanced through sleeve 88 and across the lesion in branch vessel 16. This is indicated in FIG. 11C.

It should be noted that sleeve 88, can be backloaded or preloaded onto wires 58 and 60. In any case, sleeve 88 is preferably loaded within the distal end of lumen 94 of catheter 90, and both guidewires 58 and 60 are loaded into sleeve 88 in guidewire lumen 94 of shaft 90. Once guidewires 58 and 60, and sleeve 88, are in the positions shown in FIG. 11C, device 86 is advanced over guidewires 58 and 60, and sleeve 88 (possibly with the assistance of a guide catheter—not shown) until the distal tip 102 of slit 96 is closely proximate, or adjacent, the distal tip of sleeve 88. This is illustrated in FIG. 11D. It can be seen that the distal tip of sleeve 88 is positioned at a point where guidewires 58 and 60 diverge from one another into branch vessels 14 and 16, respectively.

Device 86 is then rotated such that slit 96 engages wire 58. Device 86 is then advanced distally while wires 58 and 60 are held longitudinally in place. This causes guidewire lumen 94 to track guidewire 60, while allowing guidewire 58 to escape from guidewire lumen 94 along slit 96. Thus, as device 86 is advanced distally, the distal end of device 86 follows guidewire 60 into branch vessel 16 of bifurcation 10.

Device 86 is further advanced along guidewire 60 to a position where balloon 92 is sufficiently disposed within branch vessel 16. This is indicated in FIG. 11E.

Once balloon 92 is positioned within branch vessel 16, balloon 92 is inflated as shown in FIG. 11F. This dilates branch vessel 16. Of course, balloon 92 can be inflated and deflated any desired number of times, as is well known, in order to accomplish desired dilatation of branch vessel 16.

Balloon 92 is then deflated and device 16 is withdrawn proximally such that the distal tip 102 of slit 96 is again closely proximate the distal tip of sleeve 88 as shown in FIG. 11G. FIG. 11G also illustrates that, once tip 102 is withdrawn just proximal of the distal tip of sleeve 88, both guidewires 58 and 60 fully reside within guidewire lumen 94, since sleeve 88 also resides coaxially within guidewire lumen 94.

In order to dilate the lesion in branch vessel 14, device 86 is again rotated until slit 96 is in position to engage guidewire 60. Device 86 is then advanced distally, while holding guidewires 58 and 60 longitudinally in place. This causes guidewire lumen 94 to track along guidewire 58, while allowing guidewire 60 to escape through slit 96. Device 86 is advanced further distally until balloon 92 resides sufficiently within branch vessel 14, as illustrated in FIG. 11H.

Balloon 92 is then inflated, as shown in FIG. 11I, in order to dilate the branch vessel 14. Of course, as described with respect to branch vessel 16, balloon 92 can be inflated and deflated a desired number of times in order to accomplish sufficient dilatation. Balloon 92 is then deflated, and device 86 is withdrawn from the vasculature. Of course, device 86 can be withdrawn from the vasculature, along with guidewires 58 and 60, in a single step.

As described in the background portion of the specification, dilatation of one of branching vessels 14 or 16 can cause the other of branching vessels 14 or 16 to collapse. This is undesirable for a number of reasons. For example, if the vessel is collapsed, or even restricted, blood flow through the vessel is undesirably obstructed. Further, if the vessel collapses, it does not provide support, or back pressure, to the branch vessel being dilated. This can result in inefficient dilatation of that branch vessel.

FIGS. 12A-12C illustrate a perfusion tube 106 in accordance with one aspect of the present invention. Perfusion tube 106, in one preferred embodiment, is formed of a generally tubular structure 108 which is made of polyethylene, or another suitable polymer material. Tubular structure 108 is attached, such as by welding, adhesive, or another suitable bonding technique, to a push wire 110 which is made of stainless steel, or another suitable material. Tubular member 108 also includes a slit, or elongate aperture, 112 which extends from a proximal end 114 thereof to a distal end 116. FIG. 12B is an end view of tubular member 108 and illustrates that slit 112 extends all the way through the tubular wall of member 108. Tubular member 108 is preferably formed of a material with sufficient rigidity that the tubular member 108 will not roll up on itself about its longitudinal axis. Such rolling may be further inhibited by providing slit 112 at an angle relative to the longitudinal axis of tubular member 108, as shown in FIG. 12A.

Perfusion tube 106 can be used in much the same way as device 86 described with respect to FIGS. 10A-11I. In other words, perfusion tube 106 can be used to selectively track one of guidewires 58 and 60 into one of branch vessels 14 and 16, and then to track the other of guidewires 58 and 60 into the other branch vessels 14 and 16, without removing profusion tube 106 from the vasculature.

FIG. 12C illustrates that, in a preferred embodiment, after sheath 88 is advanced to the position shown in FIG. 11B, perfusion tube 106 is advanced over sheath 88 and rotated such that slit 112 engages guidewire 58. Profusion tube 106 is then advanced further distally, by pushing on push wire 110, such that the lumen within profusion tube 106 tracks along guidewire 60 while guidewire 58 is allowed to escape through slit 112. Of course, profusion tube 106 can be positioned to track guidewire 58 for placement within branch vessel 14. In order to accomplish such placement, push wire 110 is pulled proximally such that profusion tube 106 is withdrawn back over sleeve 88 such that both guidewires 58 and 60 are again within the lumen of tubular member 108. Profusion tube 106 is then rotated such that slit 112 engages guidewire 60, and profusion tube 106 is again advanced. This time, the lumen in profusion tube 106 tracks over guidewire 58 while allowing guidewire 60 to escape such that profusion tube 106 can be advanced into branch vessel 14.

It should also be noted that profusion tube 106 can easily be used with device 86. This is illustrated in FIGS. 13A-13C.

In one preferred embodiment, profusion tube 106 is loaded onto sleeve 88 distally of device 86. Of course, profusion tube 106 could also be loaded onto sleeve 88 proximally of device 86. However, for the sake of expedience, only the embodiment in which profusion tube 106 is loaded distally will be described in detail.

In any case, profusion tube 106 is preferably advanced over sleeve 88 until the distal end 116 of profusion tube 106 is closely proximate the distal end of sleeve 88. This is illustrated in FIG. 3A.

Then, profusion tube 106 is rotated such that slit 112 engages wire 58. Profusion tube 106 is then advanced such that it tracks guidewire 60 into branch vessel 16 while guidewire 58 is allowed to escape through slit 112.

Device 86 is then advanced distally until its distal end is closely proximate the distal end of sleeve 88. As described with respect to FIGS. 11A-11I, device 86 is rotated to a position where slit 96 engages wire 60. Device 86 is advanced distally such that guidewire lumen 94 tracks guidewire 58, allowing guidewire 60 to escape through slit 96.

By continuing to advance profusion tube 106 and device 86 as described above, profusion tube 106 will reside in branch vessel 16 while balloon 92 of device 86 will reside in branch vessel 14. This is illustrated in FIG. 13B. Balloon 92 can then be inflated to accomplish dilatation of branch vessel 14 without collapsing branch vessel 16.

Similarly, both devices can then be withdrawn proximally (while holding guidewires 58 and 60 and sleeve 88 in place) to the position shown in FIG. 13A. Profusion tube 106 is then rotated such that slot 112 engages wire 60 and so that profusion tube 106 can be advanced within branch vessel 14. Device 86 is positioned such that slit 96 engages guidewire 58 so balloon 92 can be advanced within branch vessel 16. This is indicated in FIG. 13C. Balloon 92 is then inflated to dilate branch vessel 16. Since profusion tube 106 now resides in branch vessel 14, dilatation can be accomplished without collapsing branch vessel 14.

In another preferred embodiment, profusion tube 106 can be used to accomplish dilatation as well. In that embodiment, tubular member 108 has a lumen therethrough which is sufficiently sized to receive balloon 92 in the deflated position. Both device 96 and profusion tube 106 are rotated such that slit 96 and slot 112 both engage the same guidewire (such as guidewire 60 illustrated in FIG. 13D). Balloon 92 is placed within the lumen of profusion tube 106 in the deflated position, and both balloon 92 and profusion tube 106 are placed in the same branch vessel (such as branch vessel 14). Balloon 92 is then inflated using perfusion tube 106 to exert outward pressure to dilate the chosen branch vessel. Of course, it should also be noted that a second profusion tube can also be used and inserted in the opposite branch vessel to prevent that branch vessel from collapsing during dilation.

FIG. 14A illustrates one embodiment of a dilatation and stent deployment device 120 in accordance with another aspect of the present invention. Device 120 is illustrated as an over-the-wire catheter but could be implemented in a monorail construction as well. Device 120 includes a catheter shaft 122 and balloon 124. Balloon 124 includes proximal end 126, distal end 128 and intermediate portion 130. Shaft 122 includes inflation lumen 132, first guidewire lumen 134, and second guidewire lumen 136. In one preferred embodiment (although not the preferred embodiment shown in FIGS. 14A-14C), the inflation lumen 132 and first guidewire lumen 134 are coaxially aligned with guidewire lumen 134 disposed within inflation lumen 132. Inflation lumen 132 is preferably in fluid communication with the interior of balloon 124 through aperture 138. A proximal end of shaft 122 is thus couplable to a source of fluid pressure for delivering fluid under pressure to, and withdrawing fluid from, the interior of balloon 124.

First guidewire lumen 134 is preferably configured as a conventional guidewire lumen which extends from the proximal end of catheter shaft 122 through the distal end of catheter shaft 122 (distal of balloon 124). This allows catheter shaft 122 to be advanced over guidewire 58 or 60 in a conventional manner.

In the embodiment shown in FIG. 14A, second guidewire lumen 136 also extends from the proximal end of catheter shaft 122 to a distal region of catheter shaft 122, but not all the way to the distal tip of shaft 122. Rather, the distal opening of guidewire lumen 136 is disposed in intermediate region 130 of balloon 124. Thus, guidewire 58 or 60 (guidewire 60 illustrated in FIG. 14A) exits the distal opening of guidewire lumen 136 at the intermediate portion 130 of balloon 124.

It should also be noted that device 120 can be formed in a monorail structure in which the proximal opening of each of guidewire lumens 134 and 136 do not extend all the way to the proximal end of shaft 122. In that embodiment, guidewire lumens 134 and 136 extend proximally only to a point proximal of the proximal end 126 of balloon 124.

FIG. 14B shows a greatly enlarged portion of second guidewire lumen 136 in region 140 of balloon 124. FIG. 14B illustrates that, in one preferred embodiment, a coil 142 is disposed within second guidewire lumen 136, at least in region 140 proximate balloon 124. Coil 142 can be any suitable material, such as stainless steel, surlyn, polyester, or another suitable material.

FIG. 14C illustrates a cross-sectional view of a portion of device 120 taken along section lines 14C-14C in FIG. 14A, and illustrates one preferred method of forming balloon portion 124 of device 120. A coextruded tube of balloon material is first provided with a pair of lumens therein. Interior pressure is then exerted on the portion of guidewire lumen 136 which extends through balloon 124. This causes guidewire lumen 136 to expand. Coil 142 is then placed within the expanded lumen 136 and that region of the balloon material is heated to shrink the balloon material down over coil 142 and thereby frictionally secure coil 142 within lumen 136. A hole 143 is then drilled in the side of the structural wall portion of balloon 124 in order to form the distal ostium of guidewire lumen 136.

Next, interior pressure is exerted on the interior of lumen 144 to expand lumen 144, which becomes the interior of balloon 124. Shaft 122 is then inserted through lumen 144 and the distal end 128 of balloon 124 is secured (such as with adhesive or through welding) to the distal end of shaft 122. The proximal end 126 of balloon 124 is then also secured to shaft 122 such that the portion of lumen 136 through balloon 124 communicates with the portion of lumen 136 on shaft 122. The remainder of the proximal shaft 126 of balloon 124 is then secured about the periphery of shaft 122 to form a fluid tight seal such that the interior 144 of balloon 124 can be inflated by providing pressurized fluid through inflation lumen 132.

Since coil 142 resides within lumen 136, and since lumen 136 is eccentrically arranged relative to the longitudinal axis of balloon 124, it has been observed that inflation of balloon 124 can cause balloon 124 to arc, or form a convex shape in a longitudinal direction, about coil 142 and lumen 136. This is caused because the resistance to inflation on the side of balloon 124 containing coil 142 is greater than the resistance to inflation on the opposite side of balloon 124. Therefore, in accordance with one preferred embodiment, an extra bead or portion of balloon material 146 is disposed during the extrusion process in the balloon wall on an opposite of coil 142.

This causes a balancing in resistance to the inflation force and thus reduces or eliminates any deformation of balloon 124 upon inflation.

Figure 14D:
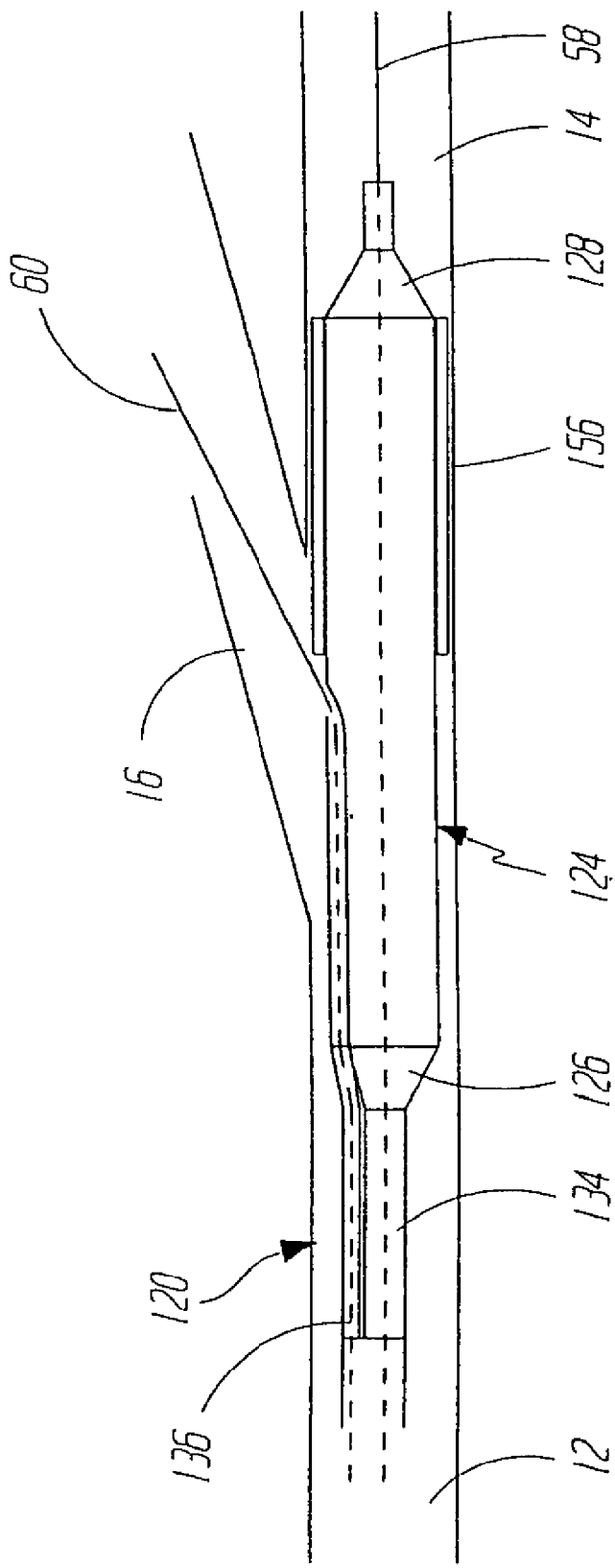

FIG. 14D illustrates operation of device 120. Guidewires 58 and 60 are first preferably advanced across lesion 18 and into branch vessels 14 and 16 as illustrated in FIG. 3. Then, device 120 is either backloaded, or preloaded, onto guidewires 58 and 60 such that one of guidewires 58 and 60 is disposed within lumen 134 and the other is disposed within lumen 136. In the illustration of FIG. 14D, guidewire 58 is disposed within lumen 134, while guidewire 60 is disposed within lumen 136.

Device 120 is then advanced distally to bifurcation 10. As device 120 is advanced distally, the distal end 128 of balloon 124 tracks along guidewire 58, because guidewire lumen 134 extends out the distal end of shaft 122. This causes the distal end 128 of balloon 124 to extend within branch vessel 14. Balloon 124 is then inflated to dilate branch vessel 14. It should also be noted, of course, that balloon 124 can be used to deploy a stent in branch vessel 14 as well, and that it can be advanced into smaller vessels as well.

FIG. 14D illustrates stent 156 disposed on the distal end of balloon 124. A stent such as stent portion 64 could also be disposed on balloon 124 with guidewire 60 extending out through aperture 68 in the wall structure of stent 64. In any case, prior to loading guidewires 58 and 60 into device 120, stent 156 is preferably crimped down over the distal portion of balloon 124 in a known manner. Balloon 124 is then loaded onto the guidewires and advanced to the position shown in FIG. 14D. Balloon 124 is then inflated to drive stent 156 to its expanded, deployed position in which it frictionally engages the inner wall of the lumen of branch vessel 14.

In order to dilate, or deploy a stent in, branch vessel 16, device 120 is withdrawn proximally and is reoriented such that guidewire 58 is disposed within lumen 136, and guidewire 60 is disposed within lumen 134. Device 120 is then advanced distally until the distal tip 128 of balloon 124 is disposed within branch vessel 16 (or in another distal vessel). Again, balloon 124 is inflated to either dilate branch vessel 16 or to deploy a stent therein.

As FIG. 14D illustrates, the proximal portion of balloon 124 will still reside in parent vessel 12 while the distal portion of balloon 124 is in either of the branch vessels 14 or 16. Thus, inflation of balloon 124 can be used to cause simultaneous dilation of parent vessel 12.

FIGS. 15A and 15B illustrate another method of forming lumen 136 in balloon 124. Rather than providing a separate lumen within the balloon wall structure of balloon 124, as illustrated in FIGS. 14A-14E, a second balloon or cavity 160 is formed within balloon 124 which comprises the portion of guidewire lumen 136 within balloon 124.

Balloon 124 is first provided. Then, a portion of balloon material is placed within balloon 124, and is inflated to form a second balloon, or cavity, 160 within balloon 124. Balloon 160 is then attached, such as through adhesive, welding or another suitable process, to the interior side wall of balloon 124. An aperture 126 is then drilled in the exterior wall of balloon 124 and into cavity 160, to form the distal ostium of guidewire lumen 136. In addition, the proximal end of balloon 160 is secured about the tube forming the proximal portion of guidewire lumen 136.

FIG. 16 illustrates another embodiment of a dilatation or stent deployment device in which the distal end of guidewire lumen 136 is formed in a different manner. In FIG. 16, sheath 164 is disposed about the proximal, exterior surface of balloon 124. Sheath 164 is secured to the exterior surface of balloon 124 throughout the entire exterior periphery of the proximal end of balloon 124 except at a region 166 which is in alignment with guidewire lumen 136. In that region, sheath 164 is not attached to the exterior surface of balloon 124. The space between the exterior surface of balloon 124 and the interior surface of sheath 164 in region 166 defines the distal region of guidewire lumen 136. It should also be noted that a tube, or other suitable material, can be inserted between balloon 124 and sheath 164 in the area of lumen 166 in order to provide additional structural integrity to the lumen.

FIG. 17 illustrates yet another embodiment of a device 170 in accordance with one aspect of the present invention. Device 170 is similar to the device illustrated in FIG. 15A. However, rather than forming a second balloon within the interior of balloon 124 in order to provide the distal region of guidewire lumen 136, device 170 illustrated in FIG. 17 includes a second balloon 168 formed on the exterior of balloon 124. Balloon 168 is coupled, by transition shaft 172, to the proximal portion of guidewire lumen 136. Balloon 168 is formed in a conventional manner, and is simply provided to define the distal region of the second guidewire lumen 136 such that it has a distal opening in the intermediate portion of balloon 124. Balloon 168 could also be made longer such that its distal end resides in the branch vessel.

Figure 18:
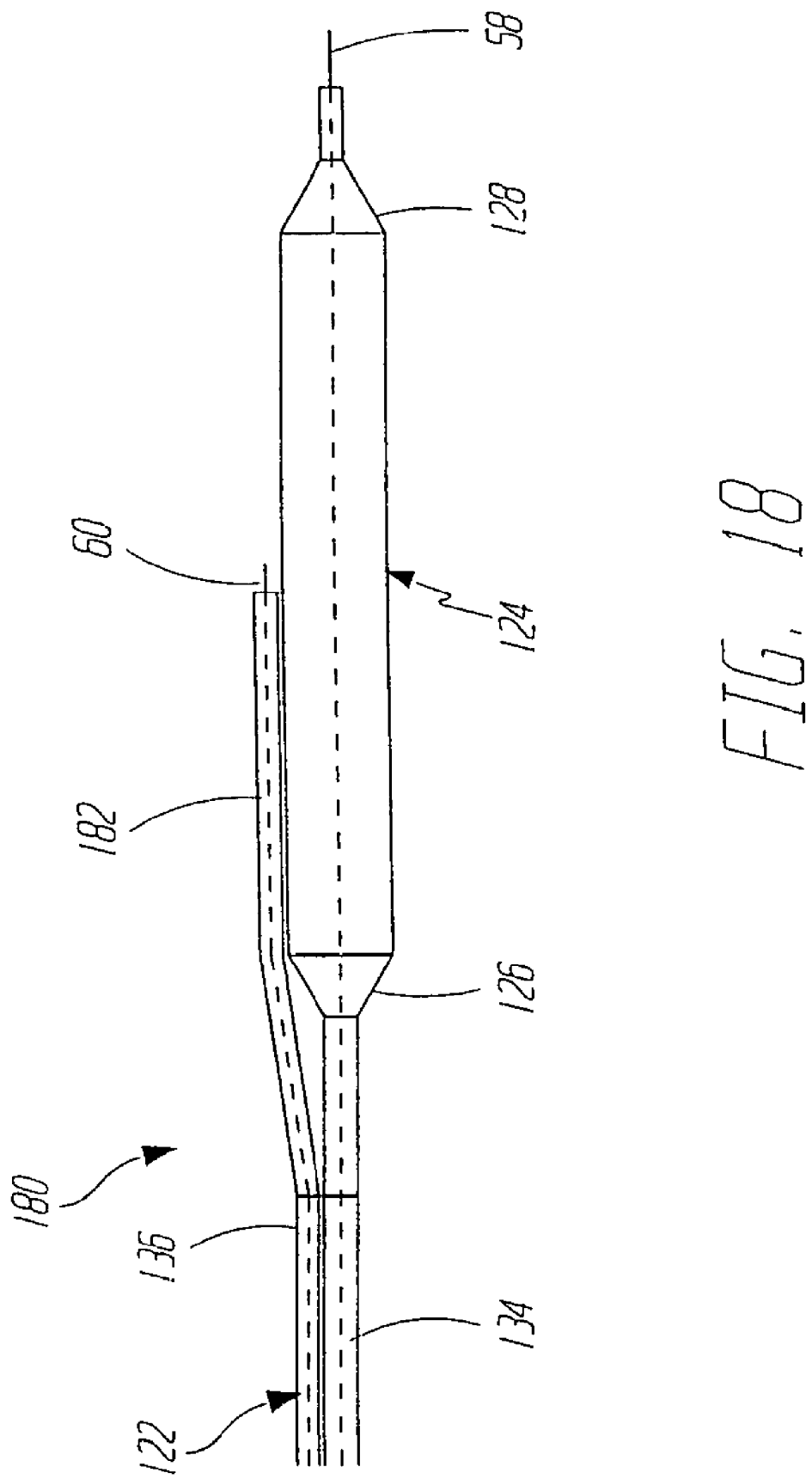

FIG. 18 illustrates yet another embodiment of a device 180 in accordance with the present invention. Device 180 is similar to device 170 shown in FIG. 17, and similar items are similarly numbered. However, rather than providing a second balloon 168 to provide the distal portion of guidewire lumen 136, device 180 simply provides a tube 182 which is connected to guidewire lumen 136 in shaft 122. Tube 182 is preferably a polyethylene tube which is a free floating tube in that it is not attached to the exterior surface of balloon 124. Tube 182 has its distal tip defining the distal opening of guidewire lumen 136 in the intermediate region of balloon 124. Tube 182 could also be made longer such that its distal opening resides in the branch vessel.

Thus, it can be seen that the present invention provides significant advantages over prior systems for performing dilatation and stent deployment at bifurcations. The present invention provides a system for simultaneously tracking two guidewires which can be positioned in the branch vessels of the bifurcation, and maintained in those branch vessels throughout the entire dilation and stent deployment. In addition, the present invention provides a system with which dilation and stent deployment can be performed in both branch vessels, without collapsing either. This reduces the cumbersome nature of performing dilation and stent deployment at bifurcations, and also enhances the efficiency of dilation and stent deployment performed in those regions.

Although the present invention has been described with reference to preferred embodiments, workers skilled in the art will recognize that changes may be made in form and detail without departing from the spirit and scope of the invention.

We claim:

1. An assembly for treatment of a vessel bifurcation comprising:
    an elongate member having a proximal end and a distal end, the elongate member defining an inflation lumen extending therethrough;
    an inflatable member having a proximal end, a distal end, and an intermediate region therebetween, the inflatable member being engaged to the elongate member adjacent the distal end of the elongate member, the inflatable member having an interior in fluid communication with the inflation lumen, wherein the inflatable member is eccentrically engaged to the entire tubular elongate member; and a guidewire sheath, the guidewire sheath defining a guidewire sheath lumen, the guidewire sheath to be moveably disposed about at least one guidewire.

2. The assembly of claim 1, further comprising a first guidewire and a second guidewire.

3. The assembly of claim 1, wherein the elongate member defines a slit, the slit in communication with the guidewire lumen, the slit extending from the distal end of the elongate member proximally to a region of the elongate member proximate a proximal end of the inflatable member.

4. The assembly of claim 1, wherein the guidewire sheath is distinct and separate from the inflation lumen.

5. The assembly of claim 1, further comprising at least one stent, the at least one stent having an unexpanded state and an expanded state, in the unexpanded state the at least one stent being disposed about at least a portion of the at least one inflatable member.

* * * * *